United States Patent
Zanini et al.

(10) Patent No.: US 7,396,890 B2
(45) Date of Patent: Jul. 8, 2008

(54) (METH)ACRYLAMIDE MONOMERS CONTAINING HYDROXY AND SILICONE FUNCTIONALITIES

(75) Inventors: Diana Zanini, Jacksonville, FL (US); Xiaoping Lin, Jacksonville, FL (US); Frank Mclock, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 11/686,729

(22) Filed: Mar. 15, 2007

(65) Prior Publication Data
US 2007/0167592 A1 Jul. 19, 2007

Related U.S. Application Data

(62) Division of application No. 10/776,739, filed on Feb. 11, 2004, now Pat. No. 7,214,809.

(51) Int. Cl.
*C08F 30/08* (2006.01)
*C08F 20/58* (2006.01)

(52) U.S. Cl. ........... 526/279; 526/264; 526/301; 526/304; 526/307.5; 526/307.7; 526/320; 526/332

(58) Field of Classification Search ......... 526/264, 526/279, 301, 304, 307.5, 307.7, 320, 332
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 3,808,178 A | 4/1974 | Gaylord | |
| 4,113,224 A | 9/1978 | Clark et al. | |
| 4,120,570 A | 10/1978 | Gaylord | |
| 4,136,250 A | 1/1979 | Mueller et al. | |
| 4,139,513 A | 2/1979 | Tanaka et al. | |
| 4,139,692 A | 2/1979 | Tanaka et al. | |
| 4,153,641 A | 5/1979 | Deichert et al. | |
| 4,182,822 A | 1/1980 | Chang | |
| 4,189,546 A | 2/1980 | Deichert et al. | |
| 4,190,277 A | 2/1980 | England | |
| 4,197,266 A | 4/1980 | Clark et al. | |
| 4,254,248 A | 3/1981 | Friends et al. | |
| 4,259,467 A | 3/1981 | Keogh et al. | |
| 4,260,725 A | 4/1981 | Keogh et al. | |
| 4,261,875 A | 4/1981 | LeBoeuf | |
| 4,276,402 A | 6/1981 | Chromecek et al. | |
| 4,327,203 A | 4/1982 | Deichert et al. | |
| 4,341,889 A | 7/1982 | Deichert et al. | |
| 4,343,927 A | 8/1982 | Chang | |
| 4,355,147 A | 10/1982 | Deichert et al. | |
| 4,450,264 A | 5/1984 | Cho | |
| 4,463,149 A | 7/1984 | Ellis | |
| 4,486,577 A | 12/1984 | Mueller et al. | |
| 4,495,313 A | 1/1985 | Larsen | |
| 4,525,563 A | 6/1985 | Shibata et al. | |
| 4,543,398 A | 9/1985 | Bany et al. | |
| 4,605,712 A | 8/1986 | Mueller et al. | |
| 4,661,575 A | 4/1987 | Tom | |
| 4,665,145 A * | 5/1987 | Yokota et al. ............... 526/279 |
| 4,680,336 A | 7/1987 | Larsen et al. | |
| 4,703,097 A | 10/1987 | Wingler et al. | |
| 4,711,943 A | 12/1987 | Harvey, III | |
| 4,837,289 A | 6/1989 | Mueller et al. | |
| 4,871,785 A | 10/1989 | Froix | |
| 4,888,406 A | 12/1989 | Ohsugi et al. | |
| 4,889,664 A | 12/1989 | Kindt-Larsen et al. | |
| 4,954,586 A | 9/1990 | Toyoshima et al. | |
| 4,954,587 A | 9/1990 | Mueller | |
| 4,980,442 A | 12/1990 | Ohsugi et al. | |
| 5,010,141 A | 4/1991 | Mueller | |
| 5,034,461 A | 7/1991 | Lai et al. | |
| 5,039,459 A | 8/1991 | Kindt-Larsen et al. | |

(Continued)

FOREIGN PATENT DOCUMENTS

EP 0131911 1/1985

(Continued)

OTHER PUBLICATIONS

Volume III, Photoinitiators for Free Radical Cationic & Anionic Photopolymerization, 2nd Edition by J.V. Crivello & K. Dietliker; edited by G. Bradley; John Wiley and Sons; New York; 1998.

*Primary Examiner*—Helen L. Pezzuto
(74) *Attorney, Agent, or Firm*—Karen Harding

(57) ABSTRACT

The present invention relates to (meth)acrylamide monomers of the formula:

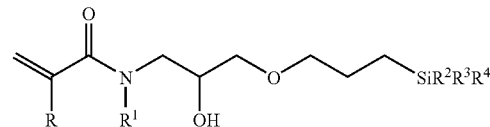

wherein R is H or $CH_3$, $R^1$ is selected from H, substituted and unsubstituted alkyl groups having 1 to 8 carbon atoms, substituted and unsubstituted benzene and toluene groups and

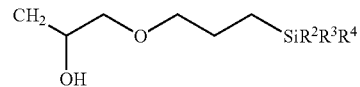

and $R^2$, $R^3$ and $R^4$ are independently selected from alkyl groups having 1 to 8 carbon atoms, substituted and unsubstituted benzene and toluene groups, and $-OSiR^5R^6R^7$ wherein $R^5$, $R^6$ and $R^7$ are independently selected from the group consisting of straight or branched alkyl groups having 1 to 4 carbon atoms. Polymers made therefrom are also disclosed.

20 Claims, No Drawings

U.S. PATENT DOCUMENTS

| | | | |
|---|---|---|---|
| 5,057,578 | A | 10/1991 | Spinelli |
| 5,070,215 | A | 12/1991 | Bambury et al. |
| 5,314,960 | A | 5/1994 | Spinelli et al. |
| 5,336,797 | A | 8/1994 | McGee et al. |
| 5,346,946 | A | 9/1994 | Yokoyama et al. |
| 5,358,995 | A | 10/1994 | Lai et al. |
| 5,371,147 | A | 12/1994 | Spinelli et al. |
| 5,387,632 | A | 2/1995 | Lai et al. |
| 5,451,617 | A | 9/1995 | Lai et al. |
| 5,486,579 | A | 1/1996 | Lai et al. |
| 5,710,302 | A | 1/1998 | Kunzler et al. |
| 5,714,557 | A | 2/1998 | Kunzler et al. |
| 5,760,100 | A | 6/1998 | Nicolson et al. |
| 5,776,999 | A | 7/1998 | Nicolson et al. |
| 5,789,461 | A | 8/1998 | Nicolson et al. |
| 5,807,944 | A | 9/1998 | Hirt et al. |
| 5,908,906 | A | 6/1999 | Kunzler et al. |
| 5,958,440 | A | 9/1999 | Burrell et al. |
| 5,962,548 | A | 10/1999 | Vanderlaan et al. |
| 5,965,631 | A | 10/1999 | Nicolson et al. |
| 5,981,615 | A | 11/1999 | Meijs et al. |
| 5,981,675 | A | 11/1999 | Valint, Jr. et al. |
| 5,998,498 | A | 12/1999 | Vanderlaan et al. |
| 6,020,445 | A | 2/2000 | Vanderlaan et al. |

FOREIGN PATENT DOCUMENTS

| | | |
|---|---|---|
| EP | 1386924 | 2/2004 |
| EP | 1439181 | 7/2004 |
| JP | 60131518 | 7/1985 |
| WO | WO 03/22321 A | 3/2003 |

* cited by examiner

(METH)ACRYLAMIDE MONOMERS CONTAINING HYDROXY AND SILICONE FUNCTIONALITIES

RELATED APPLICATIONS

This patent application is a divisional of U.S. Ser. No. 10/776,739, filed on Feb. 11, 2004, now U.S. Pat. No. 7,214,809.

FIELD OF THE INVENTION

The present invention relates to new (meth)acrylamide monomers containing hydroxy and silicone functionalities and polymers made therefrom.

BACKGROUND OF THE INVENTION

Various silicone containing monomers have found utility as starting materials in the production of medical devices, such as ophthalmic devices and particularly, soft contact lenses having improved permeability to oxygen. One class of suitable monomers includes tris and bis(trimethylsilyloxy) silylalkylglycerol methacrylates ("SiAGMA"). Another class of silicone monomers includes silicone containing vinyl carbamates. However, there remains a need in the ophthalmic device art for additional monomers which can compatibilize silicone containing monomers and macromers with hydrophilic monomers and polymers to form polymers and polymer networks which are optically clear and have desirable clinical properties such as oxygen permeability and wettability.

SUMMARY OF THE INVENTION

The present invention relates to (meth)acrylamide monomers of the formula:

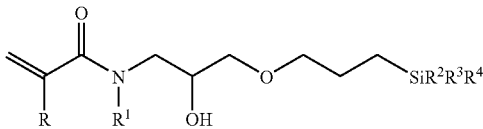

wherein R is H or $CH_3$, $R^1$ is selected from H, substituted and unsubstituted alkyl groups having 1 to 8 carbon atoms, substituted and unsubstituted benzene and toluene groups and

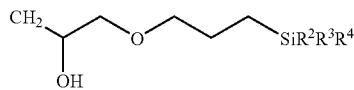

and $R^2$, $R^3$ and $R^4$ are independently selected from alkyl groups having 1 to 8 carbon atoms, substituted and unsubstituted benzene and toluene groups, and $—OSiR^5R^6R^7$ wherein $R^5$, $R^6$ and $R^7$ are independently selected from the group consisting of straight or branched alkyl groups having 1 to 4 carbon atoms.

DESCRIPTION OF THE INVENTION

The compositions of the present invention have the formula:

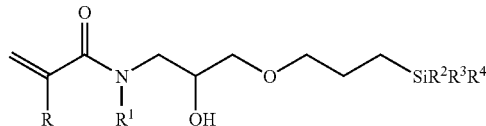

Formula I wherein R is H or $CH_3$, $R^1$ is selected from H, substituted and unsubstituted alkyl groups having 1 to 8 carbon atoms, substituted and unsubstituted benzene and toluene groups and

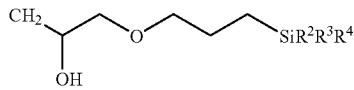

and $R^2$, $R^3$ and $R^4$ are independently selected from alkyl groups having 1 to 8 carbon atoms, substituted and unsubstituted benzene and toluene groups and $—OSiR^5R^6R^7$ wherein $R^5$, $R^6$ and $R^7$ are independently selected from the group consisting of straight or branched alkyl groups having 1 to 4 carbon atoms.

In a preferred embodiment, $R^1$ is H or an alkyl group having 1 to 3 carbon atoms and at least two of $R^2$, $R^3$ and $R^4$ are the same and are selected from alkyl groups having one to four carbons atoms and $—OSiR^5R^6R^7$ wherein $R^5$, $R^6$ and $R^7$ are independently selected from the group consisting of straight or branched alkyl groups having 1 to 4 carbon atoms. More preferably at least two of $R^2$, $R^3$ and $R^4$ are the same and are selected from methyl, ethyl, t-butyl and tri-methyl siloxy. Specific examples of (meth)acrylamide monomers include N-(2-hydroxy-3-(3-(bis(trimethylsilyloxy)methylsilyl)propyloxy)propyl)-2-methyl acrylamide; N-(2-hydroxy-3-(3-(bis(trimethylsilyloxy)methylsilyl)propyloxy)propyl) acrylamide; N,N-bis[2-hydroxy-3-(3-(bis(trimethylsilyloxy)methylsilyl)propyloxy)propyl]-2-methyl acrylamide; N,N-bis[2-hydroxy-3-(3-(bis(trimethylsilyloxy)methylsilyl)propyloxy)propyl]acrylamide; N-(2-hydroxy-3-(3-(tris(trimethylsilyloxy)silyl)propyloxy)propyl)-2-methyl acrylamide; N-(2-hydroxy-3-(3-(tris(trimethylsilyloxy)silyl)propyloxy)propyl)acrylamide; N,N-bis[2-hydroxy-3-(3-(tris(trimethylsilyloxy)silyl)propyloxy)propyl]2-methyl acrylamide; N,N-bis[2-hydroxy-3-(3-(tris(trimethylsilyloxy)silyl)propyloxy)propyl]acrylamide; N-[2-hydroxy-3-(3-(t-butyldimethylsilyl)propyloxy)propyl]-2-methyl acrylamide; N-[2-hydroxy-3-(3-(t-butyldimethylsilyl)propyloxy)propyl] acrylamide; N,N-bis[2-hydroxy-3-(3-(t-butyldimethylsilyl)propyloxy)propyl]-2-methyl acrylamide; N,N-bis[2-hydroxy-3-(3-(t-butyldimethylsilyl)propyloxy)propyl] acrylamide.

The (meth)acrylamide monomers of the present invention may be made by reacting a substituted epoxide with ammonia in the presence of an alcohol to form a hydroxy-containing amine and then reacting the hydroxy-containing amine with an acyl chloride to produce the desired (meth)acrylamide monomer. Suitable substituted expoxides include those of the formula:

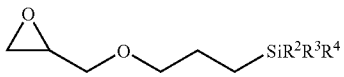

wherein $R^2$, $R^3$ and $R^4$ are defined as above. Reaction conditions for the first step comprise temperatures up to about 30° C. and reaction times from about 10 hours to about 5 days. Pressure is not critical, and ambient pressure may be used. Preferred alcohols include methanol, ethanol, and isopropanol, with methanol being preferred. The solution may be concentrated under vacuum.

The amine from the first step is reacted with an alkyl chloride such as methacryloyl chloride or acryloyl chloride, and optionally, an inhibitor. The alkyl chloride may be used in amounts ranging from equimolar to a slight excess, such as from about 1:1 to about 1: about 1.2 amine:alkyl chloride.

Any inhibitor which is capable of reducing the rate of polymerization may be used. Suitable inhibitors include hydroquinone monomethyl ether, butylated hydroxytoluene, mixtures thereof and the like. The inhibitor may be added in an amount up to about 10,000 ppm, and preferably in an amount between about 1 and about 1,000 ppm.

The reaction is conducted in a non-polar, organic solvent, such as hexane or methylene chloride, at about room temperature for a reaction time of about 12 to about 24 hours.

The resulting (meth)acrylamide monomer may be concentrated by known means, such as, but not limited to vacuum. The (meth)acrylamide monomer may be purified by various methods including acidic extraction or silica gel chromatography, treatment with ionic exchange resins, ionic exchange columns, combinations thereof and the like. Conditions for these purification methods are known in the art.

It will be appreciated by those of skill in the art that the temperature and reaction time are inversely proportional, and that higher reaction temperatures may allow for decreased reaction times and vice versa. Also, other reaction conditions which slow down the rate of reaction, such as decreased reagent concentration, may also be used in the process of the present invention.

The (meth)acrylamide monomers of the present invention may be used as a component in the manufacture of polymers formed via free radical polymerization. The (meth)acrylamide monomers of the present invention may be homopolymerized or polymerized with other monomers, prepolymers or macromers which comprise at least one polymerizable group. Suitable polymerizable groups include monovalent groups that can undergo free radical and/or cationic polymerization. Preferred polymerizable groups comprise free radical reactive groups, such as acrylates, styryls, vinyls, vinyl ethers, $C_{1-6}$alkylacrylates, acrylamides, $C_{1-6}$alkylacrylamides, N-vinyllactams, N-vinylamides, $C_{2-12}$alkenyls, $C_{2-12}$alkenylphenyls, $C_{2-12}$alkenylnaphthyls, or $C_{2-6}$alkenylphenyl$C_{1-6}$alkyls or a cationic reactive group such as vinyl ethers or epoxide groups and mixtures thereof. Particularly preferred polymerizable groups include methacrylates, acryloxys, methacrylamides, acrylamides, and mixtures thereof. In addition to the polymerizable groups, monomers, prepolymers and macromers may contain any other functionality capable of providing the polymer with the properties desired, such as elasticity, stiffness, water content, water resistance, hydrophilicity, lubricity, resistance to weathering and high temperature, combinations thereof and the like. Suitable additional functionality includes carboxylic acids, anyhydrides, esters, acyl halides, ketones, aldehydes, ethers, alcohols, amines, amides, nitriles, nitro, sulfides, mercaptans, silanes, silicones, halides, straight, branched and cyclic alkanes and alkenes, alkynes, combinations thereof and the like.

In one embodiment the polymers are hydrogel polymers such as those used in biomedical devices, such as ophthalmic devices.

In one embodiment the (meth)acrylamide monomers of the present invention are used as a component of a reactive mixture to form a silicone hydrogel. Silicone hydrogels comprise at least one (meth)acrylamide monomer, at least one hydrophilic component, and optionally at least one silicone containing component. The (meth)acrylamide monomers are particularly useful for making silicone hydrogels comprising at least one internal wetting agent. The (meth)acrylamide monomers act as compatibilizing agents, allowing both hydrophilic and silicone containing monomers to be polymerized together to form a clear article, such as an ophthalmic device.

A "compatibilizing effective amount" of the (meth)acrylamide monomers of the invention is the amount needed to dissolve the high molecular weight hydrophilic polymer and the other components of the hydrogel formulation in the selected diluent. Thus, the amount of (meth)acrylamide monomer will depend in part on the amount of internal wetting agent which is used, with more (meth)acrylamide monomer being needed to compatibilize higher concentrations of internal wetting agent. Effective amounts of (meth)acrylamide monomer in the formulation include about 5% (weight percent, based on the weight percentage of the reactive components) to about 90%, preferably about 10% to about 80%, most preferably, about 20% to about 50%.

Hydrophilic components include those which are capable of providing at least about 20% and preferably at least about 25% water content to the resulting lens when combined with the remaining reactive components. Suitable hydrophilic components may be present in amounts between about 10 to about 60 weight % based upon the weight of all reactive components, about 15 to about 50 weight % and more preferably between about 20 to about 40 weight %. The hydrophilic monomers that may be used to make the polymers of this invention have at least one polymerizable double bond and at least one hydrophilic functional group. Examples of polymerizable double bonds include acrylic, methacrylic, acrylamido, methacrylamido, fumaric, maleic, styryl, isopropenylphenyl, O-vinylcarbonate, O-vinylcarbamate, allylic, O-vinylacetyl and N-vinyllactam and N-vinylamido double bonds. Such hydrophilic monomers may themselves be used as crosslinking agents. "Acrylic-type" or "acrylic-containing" monomers are those monomers containing the acrylic group

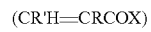

(CR'H=CRCOX)

wherein R is H or $CH_3$, R' is H, alkyl or carbonyl, and X is O or N, which are also known to polymerize readily, such as N,N-dimethylacrylamide (DMA), 2-hydroxyethyl acrylate, glycerol methacrylate, 2-hydroxyethyl methacrylamide, polyethyleneglycol monomethacrylate, methacrylic acid, acrylic acid and mixtures thereof.

Hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, N-2-hydroxyethyl vinyl carbamate, N-carboxy-β-alanine N-vinyl ester, with NVP being preferred.

Other hydrophilic monomers that can be employed in the invention include polyoxyethylene polyols having one or more of the terminal hydroxyl groups replaced with a functional group containing a polymerizable double bond. Examples include polyethylene glycol with one or more of the terminal hydroxyl groups replaced with a functional group containing a polymerizable double bond. Examples include polyethylene glycol reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,190,277. Other suitable hydrophilic monomers will be apparent to one skilled in the art.

More preferred hydrophilic monomers which may be incorporated into the polymer of the present invention include hydrophilic monomers such as N,N-dimethyl acrylamide (DMA), 2-hydroxyethyl acrylate, 2-hydroxyethyl methacrylate (HEMA), glycerol methacrylate, 2-hydroxyethyl methacrylamide, N-vinylpyrrolidone (NVP), and polyethyleneglycol monomethacrylate.

Most preferred hydrophilic monomers include HEMA, DMA, NVP and mixtures thereof.

The reactive components may optionally further comprise at least one silicone-containing component in addition to said (meth)acrylamide monomer. Suitable silicone containing components include at least one [—Si—O—Si] group, in a monomer, macromer or prepolymer. Preferably, the Si and attached O are present in the silicone-containing component in an amount greater than 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, N-vinyl lactam, N-vinylamide, and styryl functional groups. Examples of silicone components which may be included in the silicone hydrogel formulations include, but are not limited to silicone macromers, prepolymers and monomers. Examples of silicone macromers include, without limitation, polydimethylsiloxane methacrylated with pendant hydrophilic groups as described in U.S. Pat. Nos. 4,259,467; 4,260,725 and 4,261,875; polydimethylsiloxane macromers with polymerizable functional group(s) described in U.S. Pat. Nos. 4,136,250; 4,153,641; 4,189,546; 4,182,822; 4,343,927; 4,254,248; 4,355,147; 4,276,402; 4,327,203; 4,341,889; 4,486,577; 4,605,712; 4,543,398; 4,661,575; 4,703,097; 4,837,289; 4,954,586; 4,954,587; 5,346,946; 5,358,995; 5,387,632; 5,451,617; 5,486,579; 5,962,548; 5,981,615; 5,981,675; and 6,039,913; polysiloxane macromers incorporating hydrophilic monomers such as those described in U.S. Pat. Nos. 5,010,141; 5,057,578; 5,314,960; 5,371,147 and 5,336,797; macromers comprising polydimethylsiloxane blocks and polyether blocks such as those described in U.S. Pat. Nos. 4,871,785 and 5,034,461, combinations thereof and the like. All of the patents cited herein are hereby incorporated in their entireties by reference.

The silicone and/or fluorine containing macromers described in U.S. Pat. Nos. 5,760,100; 5,776,999; 5,789,461; 5,807,944; 5,965,631 and 5,958,440 may also be used. Suitable silicone monomers include tris(trimethylsiloxy)silylpropyl methacrylate, hydroxyl functional silicone containing monomers, such as 3-methacryloxy-2-hydroxypropyloxy) propylbis(trimethylsiloxy)methylsilane and those disclosed in WO03/22321, and mPDMS containing or the siloxane monomers described in U.S. Pat. Nos. 4,120,570, 4,139,692, 4,463,149, 4,450,264, 4,525,563; 5,998,498; 3,808,178; 4,139,513; 5,070,215; 5,710,302; 5,714,557 and 5,908,906.

Additional suitable siloxane containing monomers include, amide analogs of TRIS described in U.S. Pat. No. 4,711,943, vinylcarbamate or carbonate analogs described in U.S. Pat. No. 5,070,215, and monomers contained in U.S. Pat. No. 6,020,445, monomethacryloxypropyl terminated polydimethylsiloxanes, polydimethylsiloxanes, 3-methacryloxypropylbis(trimethylsiloxy)methylsilane, methacryloxypropylpentamethyl disiloxane and combinations thereof.

Silicone hydrogels of the present invention may also include an internal wetting agent, such as, but not limited to a "high molecular weight hydrophilic polymer" which refers to substances having a weight average molecular weight of no less than about 100,000 Daltons, wherein said substances upon incorporation to silicone hydrogel formulations, increase the wettability of the cured silicone hydrogels. Suitable high molecular weight hydrophilic polymers are disclosed in WO03/022321, which is incorporated in its entirety herein by reference.

Suitable amounts of high molecular weight hydrophilic polymer include from about 1 to about 15 weight percent, more preferably about 3 to about 15 percent, most preferably about 3 to about 12 percent, all based upon the total of all reactive components.

Examples of high molecular weight hydrophilic polymers include but are not limited to polyamides, polylactones, polyimides, polylactams and functionalized polyamides, polylactones, polyimides, polylactams, such as DMA functionalized by copolymerizing DMA with a lesser molar amount of a hydroxyl-functional monomer such as HEMA, and then reacting the hydroxyl groups of the resulting copolymer with materials containing radical polymerizable groups, such as isocyanatoethylmethacrylate or methacryloyl chloride. Hydrophilic prepolymers made from DMA or n-vinyl pyrrolidone with glycidyl methacrylate may also be used. The glycidyl methacrylate ring can be opened to give a diol which may be used in conjunction with other hydrophilic prepolymer in a mixed system to increase the compatibility of the high molecular weight hydrophilic polymer, hydroxyl-functionalized silicone containing monomer and any other groups which impart compatibility. The preferred high molecular weight hydrophilic polymers are those that contain a cyclic moiety in their backbone, more preferably, a cyclic amide or cyclic imide. High molecular weight hydrophilic polymers include but are not limited to poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N—N-dimethylacrylamide, polyvinyl alcohol, polyacrylic acid, polyethylene oxide, poly 2 ethyl oxazoline, heparin polysaccharides, polysaccharides, mixtures and copolymers (including block or random, branched, multichain, comb-shaped or star shaped) thereof where poly-N-vinylpyrrolidone (PVP) is particularly preferred. Copolymers might also be used such as graft copolymers of PVP.

The reaction mixtures used to make the silicone hydrogels of the present invention may also include one or more cross-linking agents, also referred to as cross-linking monomers, such as ethylene glycol dimethacrylate ("EGDMA"), trimethylolpropane trimethacrylate ("TMPTMA"), glycerol trimethacrylate, polyethylene glycol dimethacrylate (wherein the polyethylene glycol preferably has a molecular weight up to, e.g., about 5000), and other polyacrylate and polymethacrylate esters, such as the end-capped polyoxyethylene polyols described above containing two or more terminal methacrylate moieties. The cross-linking agents are used in the usual amounts, e.g., from about 0.000415 to about 0.0156 mole per 100 grams of reactive components in the reaction mixture. (The reactive components are everything in the reaction mixture except the diluent and any additional processing aids which do not become part of the structure of the polymer.) Alternatively, if the hydrophilic monomers and/or the silicone-containing monomers act as the cross-linking agent, the addition of a crosslinking agent to the reaction mixture is optional. Examples of hydrophilic monomers which can act as the crosslinking agent and when present do not require the addition of an additional crosslinking agent to the reaction mixture include polyoxyethylene polyols described above containing two or more terminal methacrylate moieties.

An example of a silicone-containing monomer which can act as a crosslinking agent and, when present, does not require the addition of a crosslinking monomer to the reaction mixture includes α, ω-bismethacryloylpropyl polydimethylsiloxane.

The reactive mixture may contain additional components such as, but not limited to, UV absorbers, medicinal agents, antimicrobial compounds, reactive tints, pigments, copolymerizable and nonpolymerizable dyes, release agents and combinations thereof.

A polymerization catalyst is preferably included in the reaction mixture. The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998, which is incorporated herein by reference. The initiator is used in the reaction mixture in effective amounts to initiate photopolymerization of the reaction mixture, e.g., from about 0.1 to about 2 parts by weight per 100 parts of reactive monomer.

The silicone hydrogels can be formed by any of the methods know to those skilled in the art. For example, the ophthalmic devices of the invention may be prepared by mixing reactive components and any diluent(s) with a polymerization initiator to form a reactive mixture and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the lens formulation in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses of this invention is by molding. For this method, the lens formulation is placed in a mold having the shape of the final desired lens, and the lens formulation is subjected to conditions whereby the components polymerize, to produce a lens. The lens may be treated with a solvent to remove the diluent and ultimately replace the diluent with water. This method is further described in U.S. Pat. Nos. 4,495,313; 4,680,336; 4,889,664; and 5,039,459, incorporated herein by reference. The preferred method of curing is with radiation, preferably UV or visible light, and most preferably with visible light.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

The dynamic contact angle or DCA, was measured at 23° C., with borate buffered saline, using a Wilhelmy balance. The wetting force between the lens surface and borate buffered saline is measured using a Wilhelmy microbalance while the sample strip cut from the center portion of the lens is being immersed into the saline at a rate of 100 microns/sec. The following equation is used $$F=2\gamma p \cos \theta \text{ or } \theta=\cos^{-1}(F/2\gamma p)$$

where F is the wetting force, γ is the surface tension of the probe liquid, p is the perimeter of the sample at the meniscus and θ is the contact angle. Typically, two contact angles are obtained from a dynamic wetting experiment—advancing contact angle and receding contact angle. Advancing contact angle is obtained from the portion of the wetting experiment where the sample is being immersed into the probe liquid, and these are the values reported herein. At least four lenses of each composition are measured and the average is reported.

The water content was measured as follows: lenses to be tested were allowed to sit in packing solution for 24 hours. Each of three test lens were removed from packing solution using a sponge tipped swab and placed on blotting wipes which have been dampened with packing solution Both sides of the lens were contacted with the wipe. Using tweezers, the test lens were placed in a weighing pan and weighed. The two more sets of samples were prepared and weighed as above. The pan was weighed three times and the average is the wet weight.

The dry weight was measured by placing the sample pans in a vacuum oven which has been preheated to 60° C. for 30 minutes. Vacuum was applied until at least 0.4 inches Hg is attained. The vacuum valve and pump were turned off and the lenses were dried for four hours. The purge valve was opened and the oven was allowed reach atmospheric pressure. The pans were removed and weighed. The water content was calculated as follows:

Wet weight = combined wet weight of pan lenses −
weight of weighing pan

Dry weight = combined dry weight of pan and lens −
weight of weighing pan $$\% \text{ water content} = \frac{(\text{wet weight} - \text{dry weight})}{\text{wet weight}} \times 100$$

The average and standard deviation of the water content are calculated for the samples are reported.

Modulus was measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width was loaded into the grips and elongated at a constant rate of strain of 2 in/min. until it broke. The initial gauge length of the sample (Lo) and sample length at break (Lf) were measured. Twelve specimens of each composition were measured and the average is reported. Tensile modulus was measured at the initial linear portion of the stress/strain curve.

The following abbreviations are used in the examples below:

SiNAA N-(2-hydroxy-3-(3-(bis(trimethylsilyloxy)methylsilyl)propyloxy)propyl)-2-methyl acrylamide SiNAA dimer N,N-bis[2-hydroxy-3-(3-(bis(trimethylsilyloxy)methylsilyl)propyloxy)propyl]-2-methyl acrylamide MEHQ hydroquinone monomethyl ether Epoxide (3-glycidoxypropyl)bis(trimethylsiloxy)methylsilane Percent conversion was determined using GC as follows. A 10 uL sample was dispersed into 1 mL IPA. The dispersed samples were analyzed using a GC-FID and conditions listed below:

Carrier Gas: Helium

Carrier Gas Pressure: 70 PSI

Total Flow: 75 mL/min

Septum purge: 3-5 mL/min

Hydrogen Pressure: 60 PSI

Air Pressure: 30 PSI

Detector: Flame ionization detector @ 280° C.

Inlet temperature: 280° C.

Autosampler wash solvent: isopropyl alcohol

Column: Restek RTX-5 30 m×0.25 mm×1.0 um (5% diphenyl, 95% dimethyl polysiloxane)

Injection Volume: 2 ul (100:1) split

Temperature Program:
 Initial Temperature: 60° C.
 Ramp: 10° C./min
 Final Temp: 325° C.
 Final time: 5 min
 Equilibrate: 7 min

EXAMPLE 1

Epoxide (50 g) was added to a thick-walled glass round bottom flask containing a magnetic stir bar at 0° C. To this was added 327 mL of 2.0 M methanolic ammonia. The flask was stoppered with a septum and stirred at room temperature (about 25° C.). After about 12 hours, a small aliquot (about 200 μL) of the reaction mixture was removed and analyzed by GC. GC revealed that the reaction still contained some Epoxide. The reaction mixture was also analyzed by thin layer chromatography (TLC) which again confirmed a small amount of Epoxide (TLC eluent: hexanes/ethyl acetate 10/1, Rf 0.65, visualized in vanillin solution). Methanolic ammonia (2M, 73 mL) was added to the solution and the solution stirred further at 25° C. After about 20 hours, GC showed only a small amount of Epoxide. TLC did not detect any of the Epoxide and did reveal the appearance of amines (a new spot at the base-line that was ninhydrin-positive, TLC eluent: hexanes/ethyl acetate 10/1). The solution was concentrated under vacuum at 55° C. to give 49.00 g of a viscous, light yellow liquid.

EXAMPLE 2

To a 250 mL, three neck round bottom flask equipped with a condenser and an additional funnel was added 32.53 g of the amine mixture from example 1, 9.4 g triethylamine, and 65 mL hexane. The solution was stirred with a magnetic stir bar. Methacryloyl chloride (10.61 g) was added drop-wise to the solution and the reaction left stirring overnight. After about 18 hours, the solution was diluted with about 200 mL hexanes and washed successively with about 250 mL de-ionized water; twice with 250 mL of 0.5 M aqueous NaOH solution, twice with about 250 mL 2.5 wt. % aqueous NaCl solution, and once with about 250 mL saturated aqueous sodium chloride solution. The pale yellow organic phase was dried over sodium sulfate and filtered. The filtrate was concentrated in vacuo to give 36.2 g of a pale yellow liquid. This yellow liquid was purified by silica gel column chromatography using ethyl aceate:hexanes, 1:4→1:2, as eluent. SiNAA and SiNAA dimer were isolated.

EXAMPLE 3

A reaction mixture was formed by adding 100 parts of the components shown in Table 1, below, in the amounts shown in Table 1 with 40 parts PVP2500:t-amyl alcohol 27.5:72.5. The reaction mixture was degassed on high vacuum, for approximately 15 minutes. The reaction mixture was dosed into thermoplastic contact lens molds, and irradiated under a nitrogen atmosphere for 30 to 150 seconds and then cured at 45 to 65° C., with an irradiation of 1.5 to 3 mW/cm$^2$, for a period of about 13 minutes. The resulting lenses were hand de-molded and underwent an aqueous hydration process as listed in Table 2. Lenses were inspected in a borate-buffered packing solution, placed in vials containing borate buffered packing solution, capped and sterilized. Physical properties were measured as described above and included a modulus of 45.2 (10.6) psi, dynamic advancing contact angle of 64° (5) and a water content of about 50.1% (0.6). The values in parenthesis are standard deviations. Accordingly, the monomer made in Example 2 may be used to produce a contact lens have desirable physical properties.

TABLE 1

| Component | Weight Percent |
|---|---|
| SiNAA | 30.00 |
| mPDMS 1000 | 22.00 |
| DMA | 31.00 |
| HEMA | 8.50 |
| EGDMA | 0.75 |
| Norbloc | 1.50 |
| Blue HEMA | 0.02 |
| PVP 360,000 | 6.00 |
| CGI 819 | 0.23 |

TABLE 2

| Hydration Solutions | Hydration Time |
|---|---|
| DI water at 70° C. (±5° C.) | 180 minutes (minimum) |
| DI water at 45° C. (±5° C.) | 30 minutes (minimum) |
| Packing Solution at room temperature | 30 minutes (minimum) |

EXAMPLE 4

A reaction mixture was formed by adding 100 parts of the components shown in Table 3, in the amounts shown in Table 3 with 40 parts PVP2500:t-amyl alcohol 27.5:72.5. The reaction mixture was degassed on high vacuum, for approximately 15 minutes. The reaction mixtures were dosed into thermoplastic contact lens molds, and irradiated under a nitrogen atmosphere for 30 to 150 seconds and then cured at 45 to 65° C., with an irradiation of 1.5 to 3 mW/cm$^2$, for a period of about 13 minutes. The resulting lenses were hand de-molded and underwent an aqueous hydration process as listed in Table 4. Lenses were inspected in a borate-buffered packing solution, placed in vials containing borate buffered packing solution, capped and sterilized. Physical properties were measured as described above and included a modulus of 52.6 (5.7) psi, dynamic advancing contact angle of 61°(6) and a water content of about 45.6% (0.1).

TABLE 3

| Component | Weight Percent |
|---|---|
| SiNAA | 30.00 |
| DMA | 20.00 |
| HEMA | 40.48 |
| EGDMA | 0.75 |
| PVP 360,000 | 7.00 |
| CGI 819 | 0.25 |
| Norbloc | 1.50 |
| Blue HEMA | 0.02 |

TABLE 4

| Hydration Solutions | Hydration Time |
|---|---|
| DI water at 95° C. (±5° C.) | 30 minutes (±5 minutes) |
| DI water at 70° C. (±5° C.) | 180 minutes (minimum) |
| DI water at 70° C. (±5° C.) | 30 minutes (minimum) |
| Packing Solution at room temperature | 30 minutes (minimum) |

EXAMPLE 5

Synthesis of 3-t-butyldimethylsilylpropyl glycidyl ether

Allyloxy glycidyl ether (50.6 g, 0.44 mol), platinic chloride (36 mg, 200 ppm) and toluene (300 mL) were charged into a one liter three-neck flask, equipped with a condenser with nitrogen inlet and outlet, and a thermocouple connected to a temperature controller. The mixture was heated up to 86° C. t-Butyldimethylsilane (50.0 g, 0.43 mol) was added dropwise to the above mixture at 86° C. with stirring. After completion of the addition of t-butyldimethylsilane, the whole mixture was stirred at 86° C. The reaction was monitored by gas chromatography. After stirring for 40 hours, the reaction solution was washed with a saturated aqueous sodium bicarbonate solution, a 5% aqueous sodium chloride solution, followed by a final wash with a saturated aqueous sodium chloride solution. The organic phase was dried over sodium sulfate and filtered. The filtrate was concentrated under reduced pressure at 45° C. to give a brownish liquid (~38 g). Pure 3-t-butyldimethylsilylpropyl glycidyl ether was obtained as a clear, colorless oil by distillation under vacuum.

EXAMPLE 6

Synthesis of 3-(3-(t-butyldimethylsilyl)propyloxy)-2-hydroxypropylamine

Methanolic ammonia (7 mol of ammonia in methanol, 100 mL, 0.7 mol,) was charged to a 500 mL, one-neck, round-bottom flask placed in an ice bath. To the above solution 3-t-butyldimethylsilylpropyl glycidyl ether (23.04 g, 0.1 mol) was added dropwise at 0° C. The mixture was allowed to warm up to room temperature and stirred for three days. The reaction solution was then warmed up to 40-50° C. to remove excess ammonia. Methanol was stripped off under reduced pressure. Crude 3-(t-butyldimethylsilylpropyloxy)-2-hydroxypropylamine was obtained as a clear and colorless oil (24 g, 98% yield).

EXAMPLE 7

Synthesis of N-[2-hydroxy-3-(3-(t-butyldimethylsilyl)propyloxy)propyl]-2-methyl acrylamide 3-(3-(t-Butyldimethylsilyl)propyloxy)-2-hydroxypropylamine (19.0 g, 0.077 mol), triethylamine (7.8 g, 10.8 mL, 0.08 mol), and methylene chloride (57 mL) were mixed in a 250 mL one-neck flask which was placed in an ice bath. To the above mixture, methacryloyl chloride (8.3 g, 7.73 mL, 077 mol) was added dropwise through an additional funnel at 0° C. After the completion of the addition of methacryloyl chloride, the whole mixture was allowed to warm up to room temperature and stirred at ambient temperature for two days. The reaction suspension was diluted with 100 mL of methylene chloride and washed with deionized water, 0.5 N sodium hydroxide aqueous solution, 5% sodium chloride solution in water twice and saturated sodium chloride aqueous solution in sequence. The organic phase was dried over sodium sulfate. After the removal of sodium sulfate by filtration, the solvent was evaporated by using a rotary evaporator under vacuum. N-[2-Hydroxy-3-(3-(t-butyldimethylsilyl)propyloxy)propyl]-2-methyl acrylamide was obtained as a white solid after purification by silica gel column chromatography.

EXAMPLE 8

Synthesis of 3-Allyloxy-2-hydroxy-propylamine

Ammonium hydroxide (28%-30% (about 14.82 mol) of ammonia in water, 202 mL, 3 mol) was charged to a one liter, one-neck, round-bottom flask that was cooled in an ice bath. To the above solution allyl glycidyl ether (57.07 g, 0.5 mol) was added dropwise at 0° C. The mixture was allowed to warm up to room temperature and stirred for two days after completion of the allyl glycidyl ether addition. 3-Allyloxy-2-hydroxy-propylamine was separated by distillation at 76° C.-82° C. under 0-1 mbar as a clear liquid (~33 g).

EXAMPLE 9

Synthesis of N-(3-Allyloxy-2-hydroxypropyl)-2-methyl acrylamide

3-Allyloxy-2-hydroxy-propylamine made in Example 8 (110 g, 0.84 mol), triethylamine (85.6 g, 0.84 mol), and methylene chloride (300 mL) were mixed in a two-liter, two-neck flask, which was placed in an ice bath. To the above mixture, methacryloyl chloride (90.36 g, 84 mol) was added dropwise through an additional funnel at 0° C. After completion of the addition of methacryloyl chloride, the whole mixture was allowed to warm up to room temperature and stirred at ambient temperature overnight (~15 hours). The reaction suspension was diluted with 250 mL of methylene chloride and washed with 5% aqueous sodium chloride solution, saturated aqueous sodium bicarbonate solution, 5% aqueous sodium chloride solution and then followed by washing with saturated aqueous sodium chloride solution. The organic phase was dried over sodium sulfate (100 g). After the removal of sodium sulfate by filtration, 4-methoxyphenol (0.5 g) was added to the filtrate. The solution was concentrated under vacuum using a rotovap to give about 122 g of crude N-(3-allyloxy-2-hydroxy-propyl)-2-methyl acrylamide. N-(3-Allyloxy-2-hydroxy-propyl)-2-methyl acrylamide was purified by distilling the raw material inhibited with 1% of 4-methoxyphenol under vacuum at 168° C.-170° C. (7-8 mbar) using Kugelrohr distillation equipment.

EXAMPLE 10

Synthesis of N-(2-hydroxy-3-(3-(tris(trimethylsilyloxy)silyl)propyloxy)propyl)-2-methyl acrylamide N-(3-Allyloxy-2-hydroxy-propyl)-2-methyl acrylamide made according to Example 9 (18 g, 0.09 mol), platinic chloride (4 mg, 100 ppm), BHT (36 mg, 2000 ppm) and toluene (90 mL) were charged into a 500 mL three-neck flask, equipped with a condenser with a nitrogen inlet and outlet, and a thermocouple connected to a temperature controller. Tris(trimethylsiloxy)silane (26.8 g, 0.09 mol) was added dropwise to the above mixture at 96-97° C. After stirred at about 96° C. for 16 hours, additional platonic chloride (4 mg, 100 ppm) was added to the reaction solution. The reaction was monitored by gas chromatography. After stirred for 47 hours, the reaction solution was washed with 0.5 N aqueous sodium hydroxide solution and twice with 2.5% aqueous sodium chloride solution. This was followed by washing with saturated aqueous sodium chloride solution. The organic phase was dried over sodium sulfate and filtered. The filtrate, inhibited with 4-methoxyphenol (0.02 g), was concentrated under reduced pressure at 30° C.-40° C. to give an oil (~36 g). N-(2-hydroxy-3-(3-(tris(trimethylsilyloxy)silyl)propyloxy)propyl)-2-methyl acrylamide was purified by column chromatography.

We claim:

1. A polymer formed from a reaction mixture comprising at least one hydrophilic monomer, at least one silicone containing component and at least one (meth)acrylamide monomer of the formula:

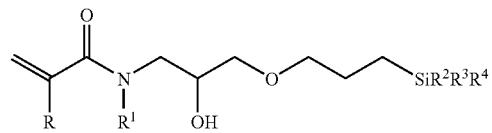

wherein R is H or $CH_3$, $R^1$ is selected from H, substituted and unsubstituted alkyl groups having 1 to 8 carbon atoms, substituted and unsubstituted benzene and toluene groups and

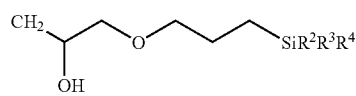

and $R^2$, $R^3$ and $R^4$ are independently selected from alkyl groups having 1 to 8 carbon atoms, substituted and unsubstituted benzene and toluene groups, and $OSiR^5R^6R^7$ wherein $R^5$, $R^6$ and $R^7$ are independently selected from the group consisting of straight or branched alkyl groups having 1 to 4 carbon atoms and wherein said polymer has a water content of at least 20%.

2. The polymer of claim 1 wherein said at least one hydrophilic monomer comprises at least one polymerizable double bond and at least one hydrophilic functional group.

3. The polymer of claim 1 wherein said at least one hydrophilic monomer is selected from the group consisting of hydrophilic vinyl-containing monomers, polyoxyethylene polyols, vinyl carbonate monomers, vinyl carbamate monomers, oxazolone monomers, and mixtures thereof.

4. The polymer of claim 1 wherein said at least one hydrophilic monomer is selected from the group consisting of N,N-dimethyl acrylamide, 2-hydroxyethyl acrylate, 2-hydroxyethyl methacrylate, glycerol methacrylate, 2-hydroxyethyl methacrylamide, N-vinylpyrrolidone, and polyethyleneglycol monomethacrylate.

5. The polymer of claim 1 wherein said at least one hydrophilic monomer is selected from the group consisting of 2-hydroxyethyl methacrylate, N,N-dimethyl acrylamide, N-vinylpyrrolidone and mixtures thereof.

6. The polymer of claim 1 wherein said at least one hydrophilic monomer is present in amounts between about 10 to about 60 weight % based upon the weight of all reactive components.

7. The polymer of claim 1 wherein said at least one hydrophilic monomer is present in an amount between about 15 to about 50 weight % based upon the weight of all reactive components.

8. The polymer of claim 1 wherein said at least one hydrophilic monomer is present in an amount between about 20 to about 40 weight % based upon the weight of all reactive components.

9. The polymer of claim 1 wherein said silicone containing component is selected from the group consisting of silicone macromers, prepolymers and monomers.

10. The polymer of claim 9 wherein said silicone containing component is a silicone macromer selected from the group consisting of polydimethylsiloxane methacrylated with pendant hydrophilic groups, polydimethylsiloxane macromers with polymerizable functional group(s), polysiloxane macromers incorporating hydrophilic monomers, macromers comprising polydimethylsiloxane blocks and polyether blocks, silicone and fluorine containing macromers and combinations thereof.

11. The polymer of claim 9 wherein said silicone containing component is a silicone monomer selected from the group consisting of tris(trimethylsiloxy)silylpropyl methacrylate, hydroxyl functional silicone containing monomers, amide analogs of TRIS, vinylcarbamate analogs, vinyl carbonate analogs, monomethacryloxypropyl terminated polydimethylsiloxanes, polydimethylsiloxanes and mixtures thereof.

12. The polymer of claim 9 wherein said silicone containing component is a silicone monomer selected from the group consisting tris(trimethylsiloxy)silylpropyl methacrylate, mPDMS and combinations thereof.

13. The polymer of claim 1 further comprising at least one internal wetting agent.

14. The polymer of claim 13 wherein said internal wetting agent comprises at least one high molecular weight hydrophilic polymer.

15. The polymer of claim 14 wherein said high molecular weight hydrophilic polymer is selected from the group consisting of polyamides, polylactones, polyimides, polylactams and functionalized polyamides, polylactones, polyimides, functionalized polylactams, hydrophilic prepolymers, and combinations thereof.

16. The polymer of claim 14 wherein said high molecular weight hydrophilic polymer is selected from the group consisting of poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinyl imidazole, poly-N-N-dimethylacrylamide, polyvinyl alcohol, polyacrylic acid, polyethylene oxide, poly 2 ethyl oxazoline, heparin polysaccharides, polysaccharides, mixtures and copolymers thereof.

17. The polymer of claim 14 wherein said high molecular weight hydrophilic polymer comprises poly-N-vinylpyrrolidone.

18. The polymer of claim 14 wherein said high molecular weight hydrophilic polymer is present in an amount between about 1 to about 15 weight percent based upon the total of all reactive components.

19. The polymer of claim 14 wherein said high molecular weight hydrophilic polymer is present in an amount between about 3 to about 15 percent, based upon the total of all reactive components.

20. The polymer of claim 1 wherein said reaction mixture further comprises additional components selected from the group consisting of crosslinking agents, photoinitiators, diluents, UV absorbers, medicinal agents, antimicrobial compounds, reactive tints, pigments, copolymerizable and non-polymerizable dyes, release agents and combinations thereof.

* * * * *

UNITED STATES PATENT AND TRADEMARK OFFICE
CERTIFICATE OF CORRECTION

| | | |
|---|---|---|
| PATENT NO. | : 7,396,890 B2 | Page 1 of 1 |
| APPLICATION NO. | : 11/686729 | |
| DATED | : July 8, 2008 | |
| INVENTOR(S) | : Diana Zanini, Ziaoping Lin and Frank Molock | |

It is certified that error appears in the above-identified patent and that said Letters Patent is hereby corrected as shown below:

On the first page, item (75), kindly delete "Frank Mclock" and insert --Frank Molock--
In Claim 1, line 32, delete "$OSiR^5R^6R^7$" and insert -- $–OSiR^5R^6R^7$--

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,396,890 B2                                   Page 1 of 1
APPLICATION NO. : 11/686729
DATED             : July 8, 2008
INVENTOR(S)       : Diana Zanini, Ziaoping Lin and Frank Molock It is certified that error appears in the above-identified patent and that said Letters Patent is hereby corrected as shown below:

On the first page, item (75), kindly delete "Frank Mclock" and insert --Frank Molock--
Column 14, in Claim 1, line 32, delete "$OSiR^5R^6R^7$" and insert -- –$OSiR^5R^6R^7$--

This certificate supersedes the Certificate of Correction issued July 14, 2009.

Signed and Sealed this

Eighteenth Day of August, 2009

David J. Kappos
*Director of the United States Patent and Trademark Office*